United States Patent
Walden et al.

(10) Patent No.: US 9,034,373 B2
(45) Date of Patent: May 19, 2015

(54) PHARMACEUTICAL SPHEROIDS

(75) Inventors: Malcolm Walden, Cambridge (GB);
Hassan Mohammad, Cambridge (GB);
Geoffrey Gerard Hayes, Cambridge (GB);
Helen Kathleen Danagher, Cambridge (GB);
Jonathon Oliver Whitehouse, Cambridge (GB)

(73) Assignee: EURO-CELTIQUE S.A., Luxembourg (LU)

(*) Notice: Subject to any disclaimer, the term of this patent is extended or adjusted under 35 U.S.C. 154(b) by 1723 days.

(21) Appl. No.: 12/225,228

(22) PCT Filed: Mar. 16, 2007

(86) PCT No.: PCT/GB2007/050129
§ 371 (c)(1),
(2), (4) Date: Oct. 19, 2009

(87) PCT Pub. No.: WO2007/105016
PCT Pub. Date: Sep. 20, 2007

(65) Prior Publication Data
US 2010/0047337 A1 Feb. 25, 2010

(30) Foreign Application Priority Data

Mar. 16, 2006 (GB) .................. 0605271.60
Mar. 20, 2006 (GB) .................. 0605542.0
Sep. 4, 2006 (GB) .................. 0617272.0

(51) Int. Cl.
A61K 9/16 (2006.01)
A61K 9/50 (2006.01)
A61K 31/485 (2006.01)

(52) U.S. Cl.
CPC ............. *A61K 9/1617* (2013.01); *A61K 9/1635* (2013.01); *A61K 9/5047* (2013.01); *A61K 31/485* (2013.01)

(58) Field of Classification Search
CPC .. A61K 31/485; A61K 9/1617; A61K 9/1635
See application file for complete search history.

(56) References Cited

U.S. PATENT DOCUMENTS 4,990,341 A * 2/1991 Goldie et al. .................. 424/484
5,458,823 A 10/1995 Perkins et al.
(Continued)

FOREIGN PATENT DOCUMENTS

EP 0271193 6/1988
EP 0654263 5/1995
(Continued)

OTHER PUBLICATIONS

Bashaiwoldu et al., "Application of dynamic mechanical analysis (DMA) to determine the mechanical properties of pellets," International Journal of Pharmaceutics 269, 2004, pp. 329-342.*
(Continued)

*Primary Examiner* — Rachael E Bredefeld
(74) *Attorney, Agent, or Firm* — Davidson, Davidson & Kappel, LLC

(57) ABSTRACT

According to the invention glyceryl monostearate and a polymeric binder are employed as a spheronising aid in the manufacture of pharmaceutical spheroids containing no or substantially no microcrystalline cellulose. The spheroids can contain one or more therapeutically active agent which undergoes no or substantially no degradation when stored under accelerated temperature and humidity conditions. A coating may be applied to the spheroids; when present, the coating is preferably a controlled release coating.

37 Claims, 4 Drawing Sheets

(56) References Cited

U.S. PATENT DOCUMENTS

| | | | |
|---|---|---|---|
| 5,638,720 | A | 6/1997 | Weinhart et al. |
| 5,807,583 | A * | 9/1998 | Kristensen et al. ............ 424/489 |
| 5,851,454 | A | 12/1998 | Rutkowski et al. |
| 5,858,411 | A * | 1/1999 | Nakagami et al. ............ 424/489 |
| 2003/0108602 | A1 * | 6/2003 | Chu et al. ....................... 424/465 |
| 2006/0153915 | A1 | 7/2006 | Park et al. |

FOREIGN PATENT DOCUMENTS

| | | |
|---|---|---|
| EP | 0826376 | 3/1998 |
| EP | 0841062 | 5/1998 |
| EP | 1161956 | 3/2000 |
| GB | 2068226 | 8/1981 |
| WO | 95/33446 | 12/1995 |
| WO | 99/13799 | 3/1999 |
| WO | 0009639 | 2/2000 |
| WO | 02/064121 | 8/2002 |
| WO | 2004064807 | 8/2004 |
| WO | 2004/100883 | 11/2004 |

OTHER PUBLICATIONS

Chopra et al., The influence of pellet shape and film coating on the filling of pellets into hard shell capsules, European Journal of Pharmaceutics and Biopharmaceutics 52, 2002, pp. 327-333.*

Remington's Pharmaceutical Sciences, 18th Edition, 1990, pp. 1635-1637.*

Gibson, M. (Ed), Pharmaceutical Preformulation and Formulation—A Practical Guide from Candidate Drug Selection to Commercial Dosage Form, Interpharm Press, 2002, ch. 11, pp. 428-431.

Ghebre-Sellassie, I. and Knock, A., Pelletization Techniques. In Swarbrick, J. and Boylan, J.C. (Eds), Encyclopedia of Pharmaceutical Technology, vol. 11, Marcel Dekker, New York, 1995, pp. 382-389.

Heng, P.W.S., Pelletization and Pellet Coating, 15th International Symposium on Microencapsulation, Parma (Italy), Sep. 18-21, 2005.

Gu, L., Liew, C.V., Heng, P.W.S., Wet Spheronization by Rotary Processing—A Multistage Single-Pot Process for Producing Spheroids, Drug Dev. Ind. Pharm., 30(2), 111-123, 2004.

Heng, P.W.S., Wan, L.S.C., Tan, Y.T.F., Relationship between aggregation of HPMC coated spheroids and tackiness/viscosity/additives of the coating formulations, Int. J. Pharm., 138 (1996), 57-66.

Wan, L.S.C., Heng, P.W.S., Liew, C.V., Spheronization conditions on spheroid shape and size, Int. J. Pharm., 96 (1993), 59-65.

Supriya, P. et al., Pelletization Techniques: A Literature Review, International Research Journal of Pharmacy 2012, 3 (3) (2012), pp. 43-47.

Bhaskaran, S., Extrusion Spheronization—A Review, International Journal of PharmTech Research, vol. 2, No. 4, pp. 2429-2433 (Oct.-Dec. 2010).

* cited by examiner

PHARMACEUTICAL SPHEROIDS

This application is a U.S. national phase application of International application No. PCT/GB2007/050129, filed Mar. 16, 2007, which claims priority to GB 0605271.6, filed Mar. 16, 2006; GB 0605542.0, filed Mar. 20, 2006; and GB 0617272.0, filed Sep. 4, 2006.

The present invention relates to a pharmaceutical composition for oral administration and to a commercial scale process for its preparation. In particular, the invention relates to a pharmaceutical composition comprising spheroids comprising glyceryl monostearate, a polymeric binder and a therapeutically active agent, and a commercial scale process for its manufacture.

BACKGROUND OF THE INVENTION

The formation of pharmaceutical spheroids using extrusion and spheronisation techniques is well known in the pharmaceutical industry and typically requires the inclusion of a spheronising aid to provide formulations with the necessary structural integrity, plasticity and water-absorbing capacity required for successful formation of spheroids.

Pharmaceutical spheroids are typically manufactured on an industrial scale by firstly mixing the active ingredient(s), spheronising aid and any other excipients in a suitably sized mixer or granulator, e.g. a Vactron 300 or a Collette Gral 300, extruding the mixture/granulate in an extruder such as a Nica E140 extruder, before spheronising the extrudate using a spheroniser, e.g. Caleva or Nica S450 spheroniser, and finally drying the resulting spheroids in a suitable dryer such as a fluid bed dryer of the type manufactured by Glatt and Aeromatic Fielder.

The spheronising aid used routinely in the pharmaceutical industry is microcrystalline cellulose.

A problem which has been observed with the use of microcrystalline cellulose is the degradation of certain drugs during prolonged storage.

For instance, we have found that in microcrystalline cellulose-containing spheroids, hydromorphone hydrochloride undergoes some degradation when stored at 25° C./60% RH. We have found that this degradation of the product is due to an incompatibility between hydromorphone hydrochloride and microcrystalline cellulose catalysed by the presence of moisture. Spheroids made mainly of microcrystalline cellulose usually retain approximately 5% moisture.

Basit et al. (1999) have reported the occurrence of instability of the highly water-soluble drug, ranitidine, when formulated as a pellet dosage form containing in excess of 60% microcrystalline cellulose, the instability involving chemical degradation of the drug by means of a complex three-way interaction between ranitidine, microcrystalline cellulose and water. The authors describe the preparation of pharmaceutical spheroids of ranitidine hydrochloride, which utilise glyceryl monostearate and barium sulphate in place of microcrystalline cellulose, using small scale laboratory equipment.

Newton et al. (2004) describe the laboratory scale preparation of pharmaceutical spheroids containing either barium sulphate or diclofenac sodium as a model drug and glyceryl monostearate as a total replacement for microcrystalline cellulose.

Chatchawalsaisin et al. (2005) describe the laboratory scale preparation of spheroids containing diclofenac sodium as a model drug and glyceryl monostearate as a total replacement for microcrystalline cellulose.

A problem with the work described by Basit et al., Newton et al. and Chatchawalsaisin et al. is that operating the processes described using industrial scale equipment results in fragmented spheroids which cannot be used commercially.

WO 00/09639 (Fuisz Technologies Limited) describes the preparation of microspheres containing fatty ester combinations and optional surfactants or emulsifiers as processing aids and active agent(s) under liquiflash conditions using the spinning devices and processes as described in U.S. Pat. Nos. 5,458,823; 5,638,720; and 5,851,454.

There exists a need in the art for alternative pharmaceutical compositions in the form of spheroids comprising a chemically-compatible spheronising aid and an active ingredient, which are free or substantially free of microcrystalline cellulose and which preferably can successfully be manufactured on an industrial scale for commercialisation. In particular, the active ingredient may be one which is sensitive to chemical degradation in the presence of microcrystalline cellulose.

Milojevic et al. (1996) describe the preparation of pellets containing glucose, microcrystalline cellulose and glyceryl monostearate by extrusion and spheronisation, and the coating of these pellets with an amylose-Ethocel® formulation using a laboratory-scale fluid bed coater.

Chopra et al. (2002) describe pellets containing paracetamol, microcrystalline cellulose, glyceryl monostearate and barium sulphate, which were produced using laboratory scale extrusion and spheronisation apparatus, before being coated with a 3% solution of ethylcellulose in ethanol containing 17.5% of povidone.

Bashaiwoldu et al. (2004) describe the production of spherical pellets containing paracetamol, microcrystalline cellulose and glyceryl monostearate by the processes of extrusion and spheronisation, and the coating of these pellets with an aqueous dispersion of ethyl cellulose-containing dibutylsebacate, oleic acid and ammonium hydroxide solution using a fluid bed coater.

There remains a further need in the art for a pharmaceutical composition in the form of coated spheroids comprising a chemically-compatible spheronising aid and an active ingredient, which are free or substantially free of microcrystalline cellulose and which preferably can successfully be made on an industrial scale for commercialisation. In particular, the active ingredient may be one which is sensitive to chemical degradation in the presence of microcrystalline cellulose.

SUMMARY OF THE INVENTION

According to the present invention, we provide pharmaceutical spheroids which comprise a matrix containing glyceryl monostearate and a polymeric binder and no or substantially no microcrystalline cellulose.

In a second aspect, the invention relates to pharmaceutical spheroids according to the invention which are provided with a coating.

In a third aspect of the invention, we provide pharmaceutical spheroids according to the invention for use as a medicament.

In a fourth aspect, the invention relates to an industrial scale process for the production of the pharmaceutical spheroids according to the invention.

In another aspect, the invention provides a method of imparting storage stability to pharmaceutical spheroids containing a therapeutically active ingredient which is sensitive to chemical degradation in the presence of microcrystalline cellulose.

It is a further aspect of the invention to provide a method of increasing the shelf life of a pharmaceutical composition comprising spheroids containing a therapeutically active ingredient which is sensitive to chemical degradation in the presence of microcrystalline cellulose.

DETAILED DESCRIPTION OF THE INVENTION

In the pharmaceutical industry, the spheronising aid used almost exclusively is microcrystalline cellulose. During wet granulation of a pharmaceutical mixture, microcrystalline cellulose can hold a significant amount of water which is necessary to produce a wet mass that has the required consistency and rheology for extrusion and spheronisation.

Spheroids made with a large microcrystalline cellulose content can retain around 5% moisture upon drying. It is this relatively high level of residual moisture which is thought to contribute to the instability of certain drugs in the presence of microcrystalline cellulose. It is therefore desirable to replace microcrystalline cellulose with an alternative spheronising aid which is chemically compatible with the drug(s) but which allows for industrial scale manufacture by extrusion/spheronisation.

We have found that by using glyceryl monostearate and a polymeric binder as a spheronising aid in the absence of microcrystalline cellulose, we can obtain spheroids which exhibit little or no chemical instability using the same extrusion and spheronisation technology and processes as used in the industrial scale production of conventional spheroids which utilise microcrystalline cellulose as a spheronising aid.

In one aspect, the present invention provides a pharmaceutical preparation comprising spheroids, the spheroids being in the form of a matrix comprising glyceryl monostearate and a polymeric binder in the absence of microcrystalline cellulose.

By "absence of microcrystalline cellulose" we mean that there is no or substantially no microcrystalline cellulose present within the matrix of the spheroids. Preferably "substantially no microcrystalline cellulose" means less than 1% w/w and more preferably less than 0.5% w/w or less than 0.25% w/w of microcrystalline cellulose based on the weight of the entire spheroid core.

If it is found that the presence of microcrystalline cellulose and water causes significant degradation of the active ingredient under long term storage conditions, e.g. 25° C./60% RH, or accelerated storage conditions, e.g. 40° C./75% RH for 3 months. The amount of microcrystalline cellulose can be reduced to a level at which significant degradation does not occur, or the microcrystalline cellulose can be eliminated altogether. Generally speaking, significant degradation may be regarded as the presence of 0.5% w/w of identified substances, or 0.2% w/w of unidentified substances related to the active ingredient, the weight basis being the original amount of the active substance.

The spheroid matrix may contain between 20 and 95% (w/w), e.g. between 30 and 95% (w/w), preferably between 50 and 95% (w/w), more preferably between 75 and 95% (w/w), and most preferably between 90 and 95% (w/w) of glyceryl monostearate, the percentage by weight being based on the weight of the entire spheroid core.

A suitable type of glyceryl monostearate for use in the manufacture of the spheroids of the present invention is glyceryl monostearate 40-55 Ph. Eur., which is available from Gattefossé as geleol pastilles. However, we currently consider that any type or grade of glyceryl monostearate may be used. Appropriate processing conditions and proportions used in any formulation of the invention may be selected by the skilled person according to the type or grade of glyceryl monostearate used.

The polymeric binders are those which when wet granulated in conjunction with glyceryl monostearate can provide a wet mass with adequate plasticity and rigidity for spheroids to be formed by extrusion/spheronisation, for example at an industrial scale. Examples of suitable polymeric binders are polyvinyl pyrollidone, e.g. Kollidon® (BASF Aktiengesellschaft), carboxypolymethylene, e.g. Carbopol® (Noveon Pharma GmbH & Co. KG), and neutral poly(ethyl acrylate, methyl methacrylate) copolymers, e.g. Eudragit® NE dispersions (Röhm GmbH & Co. KG), hydroxypropylmethyl cellulose, carboxymethyl cellulose, polyethylene oxide, polyethylene glycol, gelucire and poloxamer. Preferred polymeric binders are polyvinyl pyrollidone, carboxypolymethylene and neutral poly(ethyl acrylate, methyl methacrylate) copolymers.

When using polyvinyl pyrollidone as polymeric binder, a suitable amount is in the range of 2 to 9% (w/w), preferably 2.5 to 7.5% (w/w), and more preferably 4 to 5% (w/w) based on the total weight of uncoated spheroid, i.e. the entire spheroid core.

Where carboxypolymethylene is used as binder, a suitable amount is in the range of 0.3 to 2.5% (w/w), a preferred amount being in the range of 0.5 to 2% (w/w), a particularly preferred amount being about 1±0.25% (0.75% to 1.25%) (w/w) based on the total weight of uncoated spheroids.

During wet granulation/massing of the ingredients it is desirable that the granulate/mass produced is wetted from within and throughout the granulate/mass rather than solely on the outside of the granulate/mass. A wetting agent may be used in an amount sufficient to assist in ensuring that an evenly wetted mass is produced and to aid processing and prevent sticking of product to the walls of the mixing vessel during wet massing. Accordingly, the spheroid matrix may contain a wetting agent. Suitable wetting agents to be used in accordance with the invention include anionic sodium lauryl sulphate and non-ionic wetting agents such as polysorbates (20, 60 or 80) and sorbitan fatty acid esters. A preferred wetting agent is polysorbate 80.

One or more therapeutically active agent is usually present in the matrix of the spheroids. Any therapeutically active agent may be incorporated within the matrix; the agent can be a water soluble or water insoluble drug.

The therapeutically active agent can be selected from analgesics, anti-anginal agents, anti-arrhythmic agents, anti-bacterial agents, anti-benign prostatic hypertrophy agents, anti-coagulants, anti-depressants, anti-diabetics, anti-epileptics, anti-fungal agents, anti-gout agents, anti-hypertensive agents, anti-inflammatory agents, anti-malarials, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anthelminthics, anxiolytic agents, beta-blockers, cardiac inotropic agents, cognition enhancers, corticosteroids, cox-2-inhibitors, diuretics, erectile dysfunction improvement agents, essential and non-essential fatty acids, gastrointestinal agents, histamine receptor antagonists, hypnotics, immunosuppressants, keratolytics, leukotriene inhibitors, lipid-regulating agents, macrolides, muscle relaxants, neuroleptics, nutritional agents, opioids, protease inhibitors, sedatives, sex hormones, stimulants, and combinations and mixtures thereof. This list is not intended to be exclusive.

Preferred therapeutically active agents for inclusion in the spheroids of the invention are opioids, including opioid agonists, opioid antagonists and opioid partial agonists. For example, the following opioids may be employed in the present invention: alfentanil, allylprodine, alphaprodine, anileridine, benzylmorphine, bezitramide, buprenorphine, butorphanol, clonitazene, codeine, cyclazocine, desomorpine, dextromoramide, dezocine, diamorphine, diapromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, nalbuphine, naloxone, naltrexone, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like. The opioid may be in the form of the free base, in the form of a pharmaceutically acceptable salt or in the form of a pharmaceutically acceptable complex.

Although a therapeutically active agent may typically be used in the spheroids of the invention, spheroids containing no active agent are also envisaged, for example in the preparation of tablets by compaction of the spheroids together with active agent-containing particulates, which may or may not be in the form of spheroids. In this capacity, the spheroids may serve to restrict the active agent-containing particulates from deforming and to hold the tablet together by their own deformation during the compaction process.

The spheroids may contain up to 60% w/w or more therapeutically active agent based on the weight of uncoated spheroids. Preferably the spheroids contain up to 40%, 30%, 20%, 10% or 5% w/w of therapeutically active agent. Placebo spheroids may contain the same amount of placebo component, e.g., lactose.

A therapeutically active agent for inclusion in the spheroids of the invention may, in particular, be an active agent which is sensitive to chemical degradation in the presence of microcrystalline cellulose and moisture over prolonged storage periods, or at accelerated storage conditions, for example hydromorphone hydrochloride or ranitidine hydrochloride.

Hydromorphone hydrochloride, being an opioid analgesic which has been found to undergo chemical degradation in pharmaceutical spheroids containing both microcrystalline cellulose and moisture when stored under accelerated storage conditions, is a particularly preferred active agent for inclusion in the spheroids of the invention. Accordingly, in a preferred embodiment, spheroids of the invention are provided which contain hydromorphone hydrochloride and no or substantially no microcrystalline cellulose within the spheroid matrix; preferably these spheroids show no or substantially no degradation of the hydromorphone hydrochloride after storage, e.g. for 12, 24 or 36 months, at 25° C./60% RH or at 40° C./75% RH for 3 months.

In one preferred embodiment, the spheroids are filled into hard gelatin capsules for oral administration, each capsule containing a unit dose of a given therapeutically active agent. In a variation, the spheroids may be incorporated into other solid pharmaceutical dosage forms, for example by compression or compaction of the spheroids into tablets. Conventional tabletting excipients may also be used in the formation of the spheroids into tablets, e.g. binders, diluents, lubricants, compression aids.

In another aspect of the invention, a commercial scale process of preparing the spheroids of the invention is provided comprising the steps of:
a) forming an extrudable wet mass comprising glyceryl monostearate, water and polymeric binder;
b) extruding the wet mass;
c) spheronising the extrudate;
d) drying and sieving the resulting spheroids;
e) optionally coating the dried spheroids,
wherein the extrusion is carried out using a commercial scale extruder, e.g., a Nica E140 extruder, and the spheronisation is carried out using a commercial scale spheroniser, e.g. a Caleva or Nica S450 spheroniser.

In a further aspect of the invention we provide coated spheroids suitable for use in a pharmaceutical preparation, the coated spheroids comprising a matrix core comprising glyceryl monostearate and a polymeric binder and a coating surrounding the core.

In a preferred embodiment the matrix core of the coated spheroids contains no or substantially no microcrystalline cellulose as defined above.

A polymeric binder suitable for use in the matrix core of coated spheroids of the invention is one which when wet granulated in conjunction with glyceryl monostearate can provide a wet mass with adequate plasticity and rigidity for spheroids to be formed by extrusion and spheronisation. In this respect, examples of polymeric binders which may be used include polyvinyl pyrollidone, e.g. Kollidon® (BASF AG), carboxypolymethylene, e.g. Carbopol® (Noveon Pharma GmbH & Co. KG), and neutral poly(ethyl acrylate, methyl methacrylate) copolymers, e.g. Eudragit® NE dispersions (Röhm GmbH & Co. KG), hydroxypropylmethyl cellulose, carboxymethyl cellulose, polyethylene oxide, polyethylene glycol, gelucire and poloxamer. Preferred polymeric binders are polyvinyl pyrollidone, carboxypolymethylene and neutral poly(ethyl acrylate, methyl methacrylate) copolymers.

Suitable amounts of polyvinyl pyrollidone as binder in the preparation of the coated spheroids of the invention range from 2 to 9% (w/w), preferably from 2.5 to 7.5% (w/w), and more preferably from 4 to 5% (w/w) based on the weight of uncoated spheroids.

Suitable amounts of carboxypolymethylene as binder in the preparation of the coated spheroids of the invention are in the range of 0.3 to 2.5% (w/w), preferably in the range of 0.5 to 2% (w/w), a particularly preferred amount being 0.75 to 1.75% (w/w), most preferably being about 1% (w/w) based on the weight of uncoated spheroids.

During wet granulation/massing of the ingredients it is desirable that the granulate/mass produced is wetted from within and throughout the granulate/mass rather than solely on the outside of the granulate/mass. To assist in ensuring that an evenly wetted mass is produced, a wetting agent may be used. Accordingly, the matrix of the coated spheroids of the invention may contain a wetting agent. Suitable wetting agents are non-ionic wetting agents such as polysorbates (20, 60 and 80), sorbitan fatty acid esters and the ionic wetting agent anionic sodium lauryl sulphate. A preferred wetting agent is polysorbate 80.

The coating applied to the matrix core can be a film coating having no or substantially no ability to control release of a therapeutically active agent, for example it may perform a taste-masking function. Alternatively, or additionally, the coating may be a controlled release coating, which can either delay the onset of release of an active agent, e.g. an enteric coating, or control the release of an active agent in the gastrointestinal tract in a sustained manner over a predetermined period of time.

The coating can comprise one or more materials chosen from water insoluble waxes, e.g. cetostearyl alcohol, stearyl alcohol, hydrogenated vegetable oil, water insoluble polymers, e.g. polymethacrylates; water insoluble celluloses such as ethylcellulose and water insoluble polyvinyl acetate; water soluble polymers, e.g. polyvinyl pyrrolidone; and water soluble celluloses, e.g. hydroxypropylmethyl (HPMC) cellulose and hydroxypropyl cellulose.

Release rate modifying agents, e.g. methyl cellulose and/or carboxymethyl cellulose, can be used in the coating formulation to modify the release rate and profile of a therapeutically active ingredient.

Plasticisers such as triethyl citrate, dibutyl sebacate; and glidants such as talc and fused silica, may be added to the coating formulation to improve the quality and stability of the coat.

Various processes known in the art may be used to apply the coating to the spheroids. Thus, the coating may be applied as an aqueous dispersion of the coating material, e.g. water insoluble polymers or waxes, or as an aqueous solution of water soluble polymers, by spraying the dispersion or solution onto the spheroids using a Wurster fluidised bed system, e.g. a Wurster bottom spray coater. Alternatively, other conventional coating equipment can be used, such as a coating pan or granulator. Similarly, the coating may be applied using an organic solvent system in which the coating polymer is dispersed or dissolved in an organic solvent. Alternatively a melt congeal coating may be applied using appropriate equipment.

In one preferred embodiment the active agent is hydromorphone hydrochloride. A unit dose may comprise a capsule containing a suitable amount of spheroids in which the active agent is hydromorphone hydrochloride. Such a unit dose may exhibit in vitro dissolution rates approximating to those of capsules sold under the trade mark PALLADONE® SR in the United Kingdom, as determined by the dissolution test defined in claim 1 of European Patent No. 0271193: the dissolution rate in vitro of the dosage form, when measured by the USP Paddle Method at 100 rpm in 900 ml aqueous buffer (pH between 1.6 and 7.2) at 37° C. is between 12.5% and 42.5% (by wt) hydromorphone released after 1 hour, between 25% and 55% (by wt) hydromorphone released after 2 hours, between 45% and 75% (by wt) hydromorphone released after 4 hours and between 55% and 85% (by wt) hydromorphone released after 6 hours, the in vitro release rate being independent of pH between pH 1.6 and 7.2.

Even more preferably, the hydromorphone hydrochloride containing capsules of the invention exhibit bioequivalence to the capsules sold under the trade mark PALLADONE® SR in the United Kingdom. By "bioequivalence" it is meant that in a study in healthy subjects the 90% confidence intervals for the mean $C_{max}$ and AUC (from zero time to infinity for single doses or within a dosing interval of 12 hours at steady state) are within ±20% of those of PALLADONE® SR capsules of the same unit dose strength. The studies may be carried out as cross-over studies using e.g. 12 to 35 subjects, usually 20 to 30 subjects and preferably 24 subjects.

For example, in an open, single dose, four part, randomised crossover study to compare the pharmacokinetics of PALLADONE® SR hydromorphone HCl 4 mg controlled release capsules with other hydromorphone preparations (not according to the invention), which was completed by 24 out of 26 volunteers, the following bioavailability data was obtained for PALLADONE® SR capsules:

Mean plasma hydromorphone data (n=26)

| Time (hours) | Plasma concentration (ng/ml) |
|---|---|
| 0 | 0 |
| 0.5 | 0.03 |
| 1 | 0.17 |
| 1.5 | 0.50 |
| 2 | 0.82 |
| 2.5 | 0.98 |
| 3 | 1.04 |
| 3.5 | 1.01 |
| 4 | 0.92 |
| 4.5 | 1.00 |
| 5 | 0.87 |
| 6 | 0.68 |
| 9 | 0.47 |
| 12 | 0.42 |
| 24 | 0.32 |

Summary of Pharmacokinetics (n=24)

| PALLADONE ® SR capsule 4 mg | |
|---|---|
| AUCn (ng · h/ml) | 10.35 (1.378) |
| Cmax (ng/ml) | 1.16 (1.240) |
| Tmax (hr) | 3.0 (2.0-5.0) |
| W50 (hr) | 6.34 (2.65) |

To achieve the desired pharmacokinetics and/or bioequivalence a controlled release polymer may be employed in the spheroid coating. A preferred controlled release polymer is ethylcellulose, for example ethyl cellulose N10, preferably applied in organic solution or as an aqueous fully plasticised dispersion such as can be obtained from Colorcon under the trade name Surelease®. To achieve a uniform film coating around the spheroids and to modify the release profile, hydroxypropylmethylcellulose, may be used in the coating formulation.

It is also preferable that the coated spheroids of the present invention exhibit an in vitro release profile which approximates to that of controlled release hydromorphone hydrochloride capsules marketed in Europe under the trade name PALLADONE® SR as described herein.

The matrix of the coated spheroids may contain between 30 and 95%, preferably between 50 and 95% (w/w), more preferably between 75 and 95% (w/w), and most preferably between 90 and 95% (w/w) of glyceryl monostearate (% w/w is based on the weight of uncoated spheroids).

The matrix of the coated spheroids may contain one or more therapeutically active agents. There is no limitation on the type of therapeutically active agent(s) which may be included in the spheroid matrix, although active agents which are sensitive to chemical degradation in the presence of microcrystalline cellulose and moisture are preferred, e.g. hydromorphone hydrochloride or ranitidine hydrochloride. Furthermore, the therapeutically active agent may be water insoluble, sparingly water soluble, moderately water soluble or freely water soluble.

Thus, the therapeutically active agent(s) can be selected from analgesics, anti-anginal agents, anti-arrhythmic agents, anti-bacterial agents, anti-benign prostatic hypertrophy agents, anti-coagulants, anti-depressants, anti-diabetics, anti-epileptics, anti-fungal agents, anti-gout agents, anti-hypertensive agents, anti-inflammatory agents, anti-malarials, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anthelminthics, anxiolytic agents, beta-blockers, cardiac inotropic agents, cognition enhancers, corticosteroids, cox-2-inhibitors, diuretics, erectile dysfunction improvement agents, essential and non-essential fatty acids, gastrointestinal agents, histamine receptor antagonists, hypnotics, immunosuppressants, keratolytics, leukotriene inhibitors, lipid-regulating agents, macrolides, muscle relaxants, neuroleptics, nutritional agents, opioids, protease inhibitors, sedatives, sex hormones, stimulants, and combinations and mixtures thereof.

Other preferred therapeutically active agents for inclusion in the spheroids of the invention are opioids, including opioid agonists, opioid antagonists and opioid partial agonists, and particularly opioids which are sensitive to chemical degradation in the presence of microcrystalline cellulose and moisture over prolonged or accelerated storage periods. For example, the following opioids may be employed in the present invention: alfentanil, allylprodine, alphaprodine, anileridine, benzylmorphine, bezitramide, buprenorphine, butorphanol, clonitazene, codeine, cyclazocine, desomorpine, dextromoramide, dezocine, diamorphine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, nalbuphine, naloxone, naltrexone, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like. The opioid may be in the form of the free base, in the form of a pharmaceutically acceptable salt or in the form of a pharmaceutically acceptable complex. Hydromorphone hydrochloride is a preferred opioid for use in the coated spheroids of the invention.

Hydromorphone hydrochloride-containing spheroids, in particular such spheroids with a controlled release coating, according to the invention, will preferably have a dissolution rate in vitro, when measured by Ph. Eur. Dissolution Apparatus with E.P. baskets at 150 rpm in 900 ml 0.1% sodium lauryl sulphate at 37° C. of between 5% and 30% (by wt) hydromorphone released after 1 hour, between 44% and 65% (by wt) hydromorphone released after 2 hours, between 61% and 81% (by wt) hydromorphone released after 3 hours, between 70% and 88% (by wt) hydromorphone released after 4 hours, between 79% and 95% (by wt) hydromorphone released after 6 hours and greater than or equal to 85% (by wt) hydromorphone released after 8 hours. Preferably such spheroids contain 2 mg, 4 mg, 8 mg, 16 mg or 24 mg hydromorphone hydrochloride.

In a related aspect of the invention, a process is provided for preparing the coated spheroids of the invention comprising the following steps of:
  a) forming an extrudable wet mass comprising glyceryl monostearate, water and polymeric binder;
  b) extruding the wet mass;
  c) spheronising the extrudate;
  d) drying and sieving the resulting spheroids; and
  e) coating the dried spheroids.

Typically the glyceryl monostearate, polymeric binder and, if included, therapeutically active agent(s) are dry mixed, then formed slowly into a wet mass by the gradual addition of water, optionally within which the wetting agent is dispersed, in a planetary or a high shear mixer/granulator, such as a Gral or a Vactron. The mixer is preferably one with variable speed control and fitted with a cooling jacket around the mixing bowl to regulate the temperature of the product, e.g. to maintain it at room temperature throughout the granulation process. It is desirable to avoid melting the product in a high shear mixer (glyceryl monostearate has a relatively low melting point of 50-55° C.). Important parameters to control for successful wet granulation/massing of the pharmaceutical mixture are slow water addition rate, controllable paddle and chopper speeds and bowl temperature.

The granulate is then extruded in a commercial scale extruder, such as a Nica E140 extruder.

The resulting extrudate is spheronised using a spheroniser such as a Caleva or Nica 450 spheroniser before the resulting spheroids are dried, for example in a fluid bed dryer such as an Aeromatic Fielder or Glatt, and then, if desired, screened to obtain a suitable particle size distribution.

Finally, the dried spheroids of desired size fraction (e.g. 0.85 mm-1.8 mm) are coated with the coating formulation.

The coating material used in step e) of the process can comprise one or more materials chosen, e.g., from water insoluble waxes, water insoluble polymers, water soluble polymers, water insoluble celluloses and water soluble celluloses. A suitable coating composition comprises ethyl cellulose N10 as controlled release polymer, hydroxypropyl methyl cellulose (K100M) as release modifier and triethyl citrate as plasticiser.

In another aspect, the present invention provides a method of imparting storage stability to a pharmaceutical composition in the form of spheroids containing a therapeutically active ingredient which is sensitive to chemical degradation in the presence of microcrystalline cellulose. The method comprises the step of replacing microcrystalline cellulose with glyceryl monostearate and polymeric binder.

In a related aspect, the invention provides a method of increasing the shelf life of a pharmaceutical composition in the form of spheroids containing a therapeutically active ingredient which is sensitive to chemical degradation in the presence of microcrystalline cellulose. The method comprises the step of producing pharmaceutical spheroids in which the microcrystalline cellulose is replaced with glyceryl monostearate and polymeric binder.

REFERENCES

Figure 1:
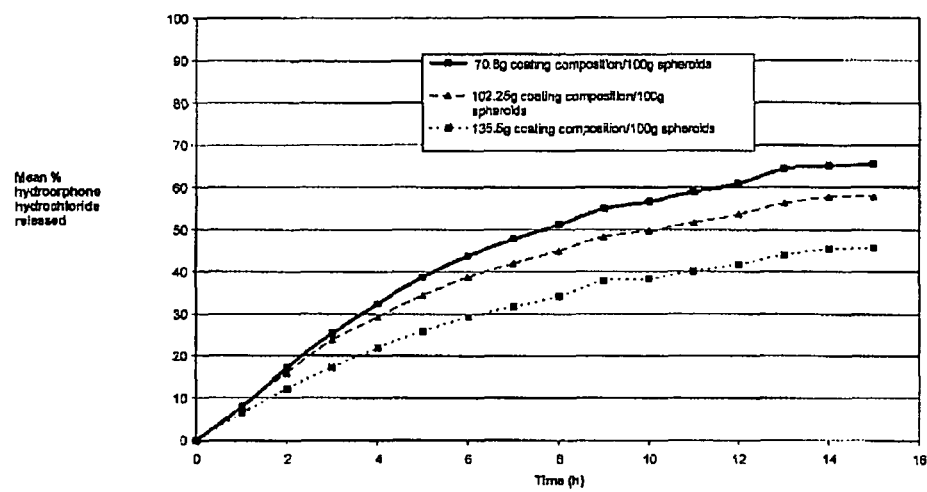
FIG. 1 shows in vitro dissolution data for the spheroid cores of Example 10 coated with various amounts of the controlled release coating composition of Example 19. The x-axis is the time in hours and the y-axis is the mean percentage of hydromorphone hydrochloride released. The continuous line with filled squares represents the results for spheroids with 70.8 g of coating composition per 100 g of spheroid cores. The dashed line with filled triangles represents the results for spheroids with 102.25 g of coating composition per 100 g of spheroid cores. The dotted line with filled squares represents the results for spheroids with 135.5 g of coating composition per 100 g of spheroid cores.

Basit, A. W, Newton, J. M, Lacey, L. F., 1999. Formulation of ranitidine pellets by extrusion-spheronization with little or no microcrystalline cellulose. Pharm. Dev. Technol. 4, 499-505.

Newton, J. M., Boutel, S., Chatchawalsaisin, J., Podczeck, F., 2004. The preparation of spherical granules by extrusion/spheronization without microcrystalline cellulose. Pharm. Technol. Eur. October 2004, 21-27.

Chatchawalsaisin, J., Podczeck, F., Newton, J. M., 2005. The preparation by extrusion/spheronization and the properties of pellets containing drugs, microcrystalline cellulose and glyceryl monostearate. Eur. J. Pharm. Sci. 24, 35-48.

Milojevic, S., Newton, J. M., Cummings, J. H., Gibson, G. R., Botham, R. L., Ring, S. G., Stockham, M., Allwood, M. C., 1996. Amylose as a coating for drug delivery to the colon: Preparation and in vitro evaluation using glucose pellets. J. Control. Release 38, 85-94.

Chopra, R., Podczeck, F., Newton, J. M., Alderborn G., 2002. The influence of pellet shape and film coating on the filling of pellets into hard shell capsules. Eur. J. Pharm. Biopharm. 53, 327-333.

Bashaiwoldu, A. B., Podczeck, F., Newton, J. M., 2004. Application of Dynamic Mechanical Analysis (DMA) to the determination of the mechanical properties of coated pellets. Int. J. Pharm. 274, 53-63.

EXAMPLES

Examples 1 to 4

Spheroids with the following placebo formulations were produced at batch size 900 g by wet granulating/massing the ingredients in a Collette Gral 10 mixer, extruding the granulate using an Alexanderwerk extruder with 1 mm cylinder holes, spheronising the extrudate with a Caleva spheroniser (750-1000 rpm for 6-10 minutes), and drying the spheroids for 60 to 90 minutes at 40 to 45° C. using an Aeromatic Strea 1 fluid bed dryer.

| Material | Example number | | | |
| --- | --- | --- | --- | --- |
| | 1 | 2 | 3 | 4 |
| | % w/w | | | |
| Lactose anhydrous | 5.00 | 5.00 | 5.00 | 5.00 |
| Glyceryl monostearate 40-55 Ph. Eur. (milled) | 75.0 | 87.5 | 90.0 | 92.5 |
| Polyvinylpyrollidone (Kollidon® 25) | 20.0 | 7.50 | 5.00 | 2.50 |
| Purified water | q.s. | q.s. | q.s. | q.s. |
| Observations | Tacky. Very Very strong. Over densified. | Very rounded spheroids. Uniform size | Spheroids not fully rounded. | High size variation |

Examples 5 to 18

Spheroid cores containing 5% (w/w) hydromorphone hydrochloride as active ingredient were prepared with the following formulations using a similar method and apparatus as for Examples 1 to 4. Glyceryl monostearate, polymeric binder and hydromorphone hydrochloride were dry mixed in a Gral 10 mixer for 3 minutes. In Examples 5 to 9 and 12 to 17, a mix of polysorbate 80 and purified water was gradually added, before further purified water sufficient to produce an evenly wetted mass was then added to the already wetted mix and mixing continued until a granulate of sufficient consistency and moisture level was formed.

| Material | Example number | | |
| --- | --- | --- | --- |
| | 5 | 6 | 7 |
| | % w/w | | |
| Hydromorphone hydrochloride | 5.00 | 5.00 | 5.00 |
| Glyceryl monostearate 40-55 Ph. Eur (milled) | 93.9 | 93.9 | 92.9 |
| Carbomer NF (Carbopol 971P) | 1.00 | 1.00 | 2.00 |
| Polysorbate 80 (Tween 80) | 0.10 | 0.20 | 0.10 |
| Purified water | q.s | q.s | q.s |

| Material | Example number | |
| --- | --- | --- |
| | 8 | 9 |
| | % w/w | |
| Hydromorphone hydrochloride | 5.0 | 5.0 |
| Glyceryl monostearate 40-55 Ph. Eur (milled) | 93.9 | 93.9 |
| Carbomer NF (Carbopol 971P) | 1.0 | 1.0 |
| Polysorbate 80 (Tween 80) | 0.1 | 0.1 |
| Purified water | | |

| Material | Example number | | | |
| --- | --- | --- | --- | --- |
| | 10 | 11 | 12 | 13 |
| | % w/w | | | |
| Hydromorphone hydrochloride | 5.00 | 5.00 | 5.0 | 5.0 |
| Glyceryl monostearate 40-55 Ph. Eur (milled) | 87.5 | 90.0 | 90.9 | 89.9 |
| Polyvinylpyrollidone (Kollidon® 25) | 7.5 | 5.0 | 4.0 | 5.0 |
| Polysorbate 80 (Tween 80) | | | 0.1 | 0.1 |
| Purified water | | | q.s. | q.s. |

-continued

| Material | Example number | | | |
|---|---|---|---|---|
| | 14 | 15 | 16 | 17 |
| | % w/w | | | |
| Hydromorphone hydrochloride | 5.00 | 5.00 | 5.0 | 5.0 |
| Glyceryl monostearate 40-55 Ph. Eur (milled) | 87.3 | 89.8 | 89.9 | 87.4 |
| Polyvinylpyrrolidone (Kollidon ® 25) | 7.50 | 5.00 | 5.00 | 7.50 |
| Polysorbate 80 (Tween 80) | 0.20 | 0.20 | 0.10 | 0.10 |
| Purified water | q.s | q.s | q.s | q.s |

| Material | Example number 18 |
|---|---|
| | % w/w |
| Hydromorphone hydrochloride | 5.00 |
| Glyceryl monostearate 40-55 Ph. Eur (milled) | 90.0 |
| Polyacrylate dispersion Eudragit NE 40 D | q.s* |
| Purified water | q.s |

Sufficient dispersion (*) was added to produce granules of appropriate consistency and moisture content for extrusion/spheronisation using the process described in the preceding Examples. Water may be added if extra moisture is required without the binding capacity/rubbery properties that the polyacrylate dispersion imparts.

Examples 19 to 21

The spheroid cores used in these Examples were from the earlier examples as follows:

Example 19: cores from Example 10
Example 20: cores from Example 11
Example 21: cores from Example 17
Example 22: cores from Example 8
Example 23: cores from Example 9

Spheroids were coated with the controlled release coatings of the following formulations:

| | Example number | | |
|---|---|---|---|
| | 19 | 20 | 21 |
| | mg/capsule | | |
| Hydromorphone-containing spheroid cores | 80 | 80 | 80 |
| | % (w/w) (based on the weight of the coating composition) | | |
| Ethyl cellulose N 10 | 4.06 | 4.06 | 4.0 |
| HPMC K100M | | | 4.0 |
| Triethyl citrate | | | 0.24 |
| Colloidal silica | 0.51 | 0.51 | |
| Dibutyl sebacate | 0.41 | 0.41 | |
| Methylene chloride* | 46.96 | 46.98 | 30.0 |
| Methanol* | 48.06 | 48.05 | 61.8 |
| Quantity of coating material applied to the spheroids (g coating composition/100 g spheroid cores) | 70.8; 102.25; 135.5 | 100; 165; 180 | 100; 150; 180 |

| | Example number | |
|---|---|---|
| | 22 | 23 |
| | mg/capsule | |
| Hydromorphone-containing spheroid cores | 80 | 80 |
| | % (w/w) (based on the weight of the coating composition) | |
| Ethyl cellulose N10 | 5.0 | 5.0 |
| HPMC K100M | 3.0 | 3.0 |
| Triethyl citrate | 0.24 | 0.24 |
| Methylene chloride* | 30.0 | 30.0 |
| Methanol* | 61.80 | 61.80 |
| Quantity of coating material applied to the spheroids (g coating composition/100 g spheroid cores | 50; 75; 100 | |

*removed by drying

All of the above batches were coated using the small scale Strea 1 Aeromatic. Batch size was typically 300 g. The quantity of coating material applied was in the range of 50 g to 300 g coating solution per 100 g of spheroid core(s) and may vary from batch to batch depending on the coating formulation used and the release profile that was desired. The weight gains may be from 3% to 15% (w/w) of weight of uncoated spheroids. The coating conditions were as follows: 1.0 mm spray gun, Wurster column, 10 mm above flat surface, 1.6 mm tubing, atomising pressure typically 1.5 bar, inlet temperature 40-45° C., outlet temperature 25-30° C., fan capacity 80-100 m³/hr.

The batches were first undercoated with HPMC E5 or Eudragit EPO before the coatings set forth in the tables above were applied.

Figure 2:
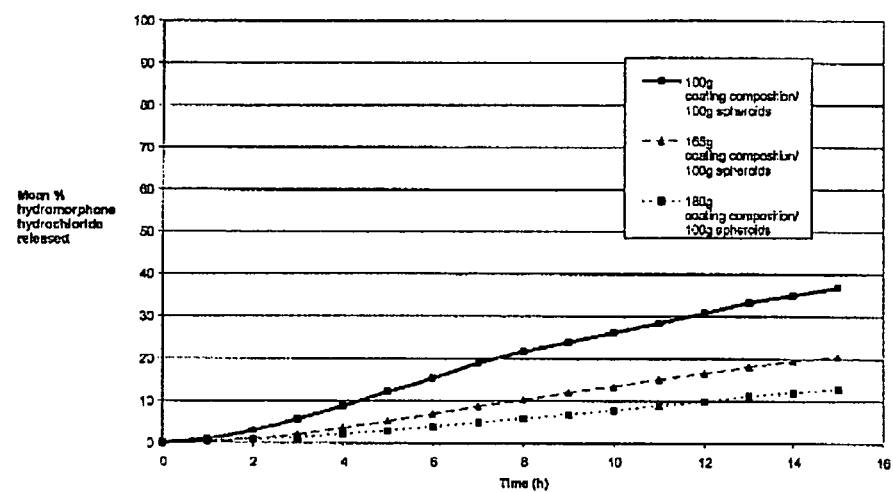
FIG. 2 shows in vitro dissolution data for the spheroid cores of Example 11 coated with various amounts of the controlled release coating composition of Example 20. The x-axis is the time in hours and the y-axis is the mean percentage of hydromorphone hydrochloride released. The continuous line with filled squares represents the results for spheroids with 100 g of coating composition per 100 g of spheroid cores. The dashed line with filled triangles represents the results for spheroids with 165 g of coating composition per 100 g of spheroid cores. The dotted line with filled squares represents the results for spheroids with 180 g of coating composition per 100 g of spheroid cores.
Figure 3:
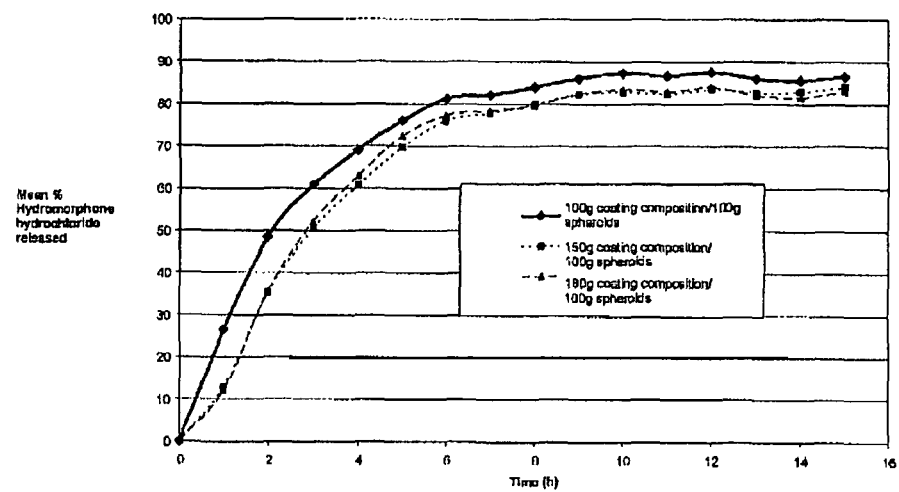
FIG. 3 shows in vitro dissolution data for the spheroid cores of Example 17 coated with various amounts of the controlled release coating composition of Example 21. The x-axis is the time in hours and the y-axis is the mean percentage of hydromorphone hydrochloride released. The continuous line with filled diamonds represents the results for spheroids with 100 g of coating composition per 100 g of spheroid cores. The dotted line with filled squares represents the results for spheroids with 150 g of coating composition per 100 g of spheroid cores. The dashed line with filled diamonds represents the results for spheroids with 180 g of coating composition per 100 g of spheroid cores.
Figure 4:
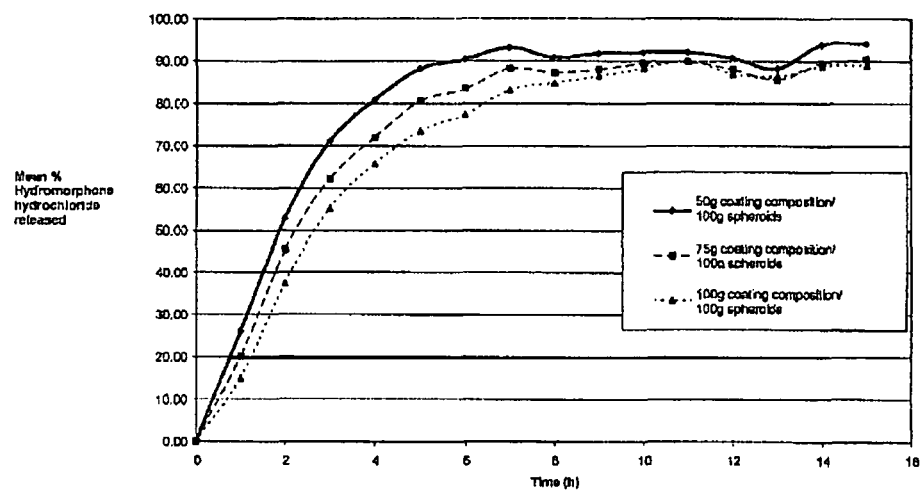
FIG. 4 shows some in vitro dissolution data for the spheroid cores of Example 8 coated with various amounts of the controlled release coating composition of Example 22. The x-axis is the time in hours and the y-axis is the mean percentage of hydromorphone hydrochloride released. The continuous line with filled diamonds represents the results for spheroids with 50 g of coating composition per 100 g of spheroid cores. The dashed line with filled squares represents the results for spheroids with 75 g of coating composition per 100 g of spheroid cores. The dotted line with filled triangles represents the results for spheroids with 100 g of coating composition per 100 g of spheroid cores.

The spheroids according to Examples 19, 20, 21 and 22 were tested by the dissolution method described above which utilises 900 ml 0.1% sodium lauryl sulfate at 37° C. and the results are shown in FIGS. 1, 2, 3 and 4, wherein the respective coating weights are indicated.

We have found that such undercoating is not essential to obtain spheroids with well controlled release after accelerated storage and that drying for 1 hour after coating with the controlled release coating to remove solvent residues and stabilise the cores can be adequate.

Example 24

Example 8 was repeated using Nica 140 extruder and Nica 450 spheroniser. The spheroids were sieved and those in the size range 0.85 mm to 1.8 mm diameter were collected.

Example 25

Development Stability Batches

Spheroids having the following compositions were prepared by the methods described above.

Spheroid Cores

| Material | % w/w |
|---|---|
| Hydromorphone hydrochloride | 5.0 |
| Glyceryl monostearate 40-55 Ph. Eur (milled) | 93.9 |
| Carbomer NF (Carbopol 971P) | 1.0 |
| Polysorbate 80 (Tween 80) | 0.1 |
| Purified water | q.s |

The resulting spheroids were coated with the following compositions, using the methods described above.

| Example 25 | |
|---|---|
| | mg/capsule |
| Hydromorphone-containing spheroid cores | 80 |
| | % (w/w) (based on the weight of the coating composition) |
| Ethyl cellulose N10 | 5.0 |
| HPMC K100M | 3.0 |
| Triethyl citrate | 0.24 |
| Methylene chloride* | 30.0 |
| Methanol* | 61.8 |

*removed by drying

The coated spheroids were sieved and those in the size range 0.85 mm to 1.8 mm diameter were collected. The collected spheroids were then filled into hard gelatin capsules to give a filling corresponding to 4 mg hydromorphone hydrochloride in each capsule.

The capsules were stored in open and closed high density polyethylene bottles (bottles closed with low density polypropylene caps) for 8 weeks under accelerated storage conditions at 40° C./75% RH and then assayed for degradation products after this period. The results were as follows:

| | Open bottles | | Closed bottles | |
|---|---|---|---|---|
| Storage conditions | Initial | 8 weeks 40° C./75% RH | Initial | 8 weeks 40° C./75% RH |
| Assay (mg active/capsule) | 4.09 | 4.04 | 4.09 | 3.94 |
| Degradation products (%)* | 0.00 | 0.06 | 0.00 | 0.00 |
| Total degradation products % (w/w) | 0.00 | 0.06 | 0.00 | 0.00 |

Limit of Quantitation (LOQ) = 0.05%
*The weight basis of the degradation products is the original weight of the active ingredient.

The invention claimed is:

1. A pharmaceutical preparation comprising spheroids obtained by extrusion and spheronisation, the spheroids comprising a matrix core comprising (1) as a spheronising aid, between 50 and 95% w/w of glyceryl monostearate, the percentage by weight being based on the weight of the entire spheroid core, (2) a polymeric binder selected from the group consisting of polyvinyl pyrrolidone, carboxypolymethylene, acrylic polymers, hydroxypropylmethyl cellulose, carboxymethyl cellulose, polyethylene oxide, polyethylene glycol, and poloxamer, and (3) hydromorphone or a pharmaceutically acceptable salt thereof, wherein the matrix core contains no or substantially no microcrystalline cellulose.

2. A pharmaceutical preparation according to claim 1, wherein the matrix core further comprises a wetting agent.

3. A pharmaceutical preparation according to claim 2, wherein the wetting agent is polysorbate 80.

4. A pharmaceutical preparation according to claim 1, which comprises hydromorphone hydrochloride.

5. A pharmaceutical preparation according to any one of claims 1-3 or 4, wherein the preparation is in the form of a capsule containing a plurality of said spheroids and being suitable for oral administration.

6. A pharmaceutical preparation according to any one of claims 1 to 3 or 4, wherein the preparation is in the form of a tablet comprising the spheroids and tabletting excipients.

7. A pharmaceutical unit dosage form comprising spheroids as defined in claim 1, the unit dosage form containing 4 mg hydromorphone hydrochloride and, when administered to healthy subjects, in a single dose study, providing a mean $C_{max}$ and a mean $AUC_{0\text{-}infinity}$, the 90% confidence intervals for which are within ±20% of 1.16 ng/ml and 10.35 ng.h/ml, respectively.

8. Spheroids suitable for use in a pharmaceutical preparation comprising a matrix core comprising (1) as a spheronising aid, between 50 and 95% w/w of glyceryl monostearate, the percentage by weight being based on the weight of the entire core, (2) a polymeric binder selected from the group consisting of polyvinyl pyrrolidone, carboxypolymethylene, acrylic polymers, hydroxypropylmethyl cellulose, carboxymethyl cellulose, polyethylene oxide, polyethylene glycol, and poloxamer, (3) hydromorphone or a pharmaceutically acceptable salt thereof, and (4) optionally a coating surrounding the core, wherein the spheroids are obtained by extrusion and spheronisation, and the matrix core contains no or substantially no microcrystalline cellulose.

9. Spheroids according to claim 8, wherein the matrix core further comprises a wetting agent.

10. Spheroids according to claim 9, wherein the wetting agent is polysorbate 80.

11. Spheroids according to claim 8, wherein the coating is a film coating having no or substantially no release controlling property.

12. Spheroids according to claim 8, wherein the coating is a controlled release coating.

13. Spheroids according to claim 12, wherein the coating comprises one or more materials chosen from water insoluble waxes, water insoluble polymers, water soluble polymers, water insoluble celluloses and water soluble celluloses.

14. Spheroids according to claim 13, wherein the water insoluble polymers comprise polymethacrylates.

15. Spheroids according to claim 13, wherein the water insoluble celluloses comprise ethylcellulose.

16. Spheroids according to claim 13, wherein the water soluble polymers comprise polyvinyl pyrrolidone.

17. Spheroids according to claim 13, wherein the water soluble celluloses comprise hydroxypropylmethyl cellulose and hydroxypropyl cellulose.

18. Spheroids according to claim 13, wherein the water insoluble waxes are selected from the group consisting of cetostearyl alcohol, stearyl alcohol, and hydrogenated vegetable oil.

19. Spheroids according to claim 13, wherein the water insoluble polymers comprise water insoluble polyvinyl acetate.

20. Spheroids according to claim 8, wherein the matrix core contains from 75 to 95% w/w glyceryl monostearate.

21. Spheroids according to claim 20, wherein the matrix core contains from 90 to 95% w/w glyceryl monostearate.

22. Spheroids according to claim 8, wherein the polymeric binder is selected from the group consisting of polyvinyl pyrrolidone, carboxypolymethylene and acrylic polymers.

23. Spheroids according to claim 8, wherein the matrix core contains from 2 to 9% w/w polyvinyl pyrrolidone.

24. Spheroids according to claim 23, wherein the matrix core contains from 2.5% to 7.5% w/w polyvinyl pyrrolidone.

25. Spheroids according to claim 24, wherein the matrix core contains from 4% to 5% w/w polyvinyl pyrrolidone.

26. A pharmaceutical unit dosage form comprising spheroids as defined in claim 8, the unit dosage form containing 4 mg hydromorphone hydrochloride and, when administered to healthy subjects, in a single dose study, providing a mean $C_{max}$ and a mean $AUC_{0-infinity}$, the 90% confidence intervals for which are within ±20% of 1.16 ng/ml and 10.35 ng.h/ml, respectively.

27. Spheroids obtained by extrusion and spheronisation containing (1) between 50 and 95% (w/w) of glyceryl monostearate, (2) a polymeric binder selected from the group consisting of polyvinyl pyrrolidone, carboxypolymethylene, acrylic polymers, hydroxypropylmethyl cellulose, carboxymethyl cellulose, polyethylene oxide, polyethylene glycol, and poloxamer, (3) hydromorphone hydrochloride, and (4) optionally a wetting agent and no microcrystalline cellulose, surrounded by a controlled release coating comprising one or more materials chosen from water insoluble waxes, water insoluble polymers, water insoluble celluloses, water soluble polymers and water soluble celluloses.

28. A pharmaceutical unit dosage form comprising spheroids as defined in any one of claim 1-3, 4, 8, 9-17, 20-25 or 27, the unit dosage form containing 2 mg, 4 mg, 8 mg, 16 mg, or 24 mg hydromorphone hydrochloride.

29. A pharmaceutical unit dosage form comprising spheroids as defined in claim 27, the unit dosage form containing 4 mg hydromorphone hydrochloride and, when administered to healthy subjects, in a single dose study, providing a mean $C_{max}$ and a mean $AUC_{0-infinity}$, the 90% confidence intervals for which are within ±20% of 1.16 ng/ml and 10.35 ng.h/ml, respectively.

30. Spheroids according to claim 27, wherein the water insoluble waxes are selected from the group consisting of cetostearyl alcohol, stearyl alcohol, and hydrogenated vegetable oil.

31. Spheroids according to claim 27, wherein the water insoluble polymers are selected from the group consisting of polymethacrylates and water insoluble polyvinyl acetate.

32. Spheroids according to claim 27, wherein the water insoluble celluloses comprise ethylcellulose.

33. Spheroids according to claim 27, wherein the water soluble polymers comprise polyvinyl pyrrolidone.

34. Spheroids according to claim 27, wherein the water soluble celluloses are selected from the group consisting of hydroxypropylmethyl cellulose and hydroxypropyl cellulose.

35. A process for preparing spheroids comprising the steps of:
   a) forming an extrudable wet mass comprising (1) between 50 and 95% w/w of glyceryl monostearate, (2) hydromorphone or a pharmaceutically acceptable salt thereof, (3) water, and (4) a polymeric binder selected from the group consisting of polyvinyl pyrrolidone, carboxypolymethylene, acrylic polymers, hydroxypropylmethyl cellulose, carboxymethyl cellulose, polyethylene oxide, polyethylene glycol, and poloxamer;
   b) extruding the wet mass to form an extrudate;
   c) spheronising the extrudate to form spheroids;
   d) drying and sieving the resulting spheroids;
   wherein the process is carried out on a commercial scale, and the formed spheroids contain no or substantially no microcrystalline cellulose.

36. A process for preparing spheroids comprising the steps of:
   a) forming an extrudable wet mass comprising (1) between 50 and 95% w/w of glyceryl monostearate, (2) hydromorphone or a pharmaceutically acceptable salt thereof, (3) water and (4) a polymeric binder selected from the group consisting of polyvinyl pyrrolidone, carboxypolymethylene, acrylic polymers, hydroxypropylmethyl cellulose, carboxymethyl cellulose, polyethylene oxide, polyethylene glycol, and poloxamer;
   b) extruding the wet mass to form an extrudate;
   c) spheronising the extrudate to form spheroids;
   d) drying and sieving the resulting spheroids;
   e) coating the dried spheroids with a coating material;
   wherein the process is carried out on a commercial scale, and the formed spheroids contain no or substantially no microcrystalline cellulose.

37. A process according to claim 36, wherein the coating material comprises one or more materials selected from the group consisting of water insoluble waxes, water insoluble polymers, water soluble polymers, water insoluble celluloses and water soluble celluloses.

\* \* \* \* \*